United States Patent
Kovelman

[11] Patent Number: 5,964,731
[45] Date of Patent: Oct. 12, 1999

[54] DISPOSABLE, DISABLING SAFETY NEEDLE FOR A SYRINGE, PEN-TYPE INJECTOR, OR THE LIKE, AND METHOD OF MAKING THE SAME

[76] Inventor: Paul H. Kovelman, 5344 Seneca Place, Simi Valley, Calif. 93063

[21] Appl. No.: 08/942,801

[22] Filed: Oct. 2, 1997

[51] Int. Cl.[6] .................................................. A61M 5/32
[52] U.S. Cl. .......................... 604/110; 604/192; 604/198
[58] Field of Search .................................. 604/110, 192, 604/187, 198, 263

[56] References Cited

U.S. PATENT DOCUMENTS

| | | | |
|---|---|---|---|
| 5,254,100 | 10/1993 | Huband | 604/198 |
| 5,267,977 | 12/1993 | Feeney | 604/198 |
| 5,279,579 | 1/1994 | D'Amico | 604/192 |
| 5,643,222 | 7/1997 | Mahurkar | 604/198 X |
| 5,713,873 | 2/1998 | Jehle | 604/198 |
| 5,743,888 | 4/1998 | Wilkes et al. | 604/198 |

Primary Examiner—John D. Yasko
Attorney, Agent, or Firm—Paul H. Kovelman

[57] ABSTRACT

A piercing member assembly, such as a needle assembly, a lancet assembly, or the like, includes a piercing member, a piecing member base, a slidable piercing member cover and a rotatable piercing member collar. The piercing member base holds and secures the piecing member in place so that it can be used. The slidable piercing member cover is non-rotatively coupled to the piercing member base to slide over and cover the piercing member resulting in the disabling piercing assembly being disabled. The rotatable piercing member collar is rotatably coupled to the piercing member base and the slidable piercing member cover so that when the rotatable piercing member collar is rotated relative to the piercing member base and the slidable piercing member cover, the slidable piercing member cover slides over and covers the piercing member to disable the disabling piercing assembly.

9 Claims, 3 Drawing Sheets

DISPOSABLE, DISABLING SAFETY NEEDLE FOR A SYRINGE, PEN-TYPE INJECTOR, OR THE LIKE, AND METHOD OF MAKING THE SAME

FIELD OF THE INVENTION

This invention relates to disabling needles and, in particular embodiments, to a disposable, disabling needle for a syringe, pen-type injector, or the like, that has improved disabling and safety characteristics.

BACKGROUND OF THE INVENTION

Traditionally, disposable needles have been used with syringes and pen-type injectors and are prevalently used worldwide on reusable or multi-dose devices for invasive delivery of medication. However, because a needle is an invasive device, after a use on a patient, the needle may become a deadly transmitter of infectious diseases, such as Acquired Immune Deficiency Syndrome (AIDS), hepatitis or the like. Thus, replaceable needles present a growing and ever-present health hazard to users in either institutional or home use settings. In addition, used, discarded needles pose a real threat to anyone coming in contact with them In the past, safe disposal of used needles has been left entirely to the user. For example, conscientious disposal of needles entails an elaborate and often dangerous procedure. First, the needle is unscrewed and removed from the syringe or pen-type injector, then the needle point is manually broken with a specially designed device; and the needle is disposed of in a special canister designed for safe storage and transportation of contaminated waste products. However, this procedure provides numerous opportunities for contact with a used needle and increases the chance of being accidentally stuck by these potentially contaminated needles. Also, the special canister itself, once filled with exposed needle points, is itself a health and safety hazard.

SUMMARY OF THE DISCLOSURE

It is an object of an embodiment of the present invention to provide an improved disposable, disabling safety needle, which obviates for practical purposes, the above-mentioned limitations.

According to an embodiment of the invention, a piercing member assembly, such as a needle assembly, a lancet assembly, or the like, includes a piercing member, a piercing member base, a slidable piercing member cover and a rotatable piercing member collar. The piercing member base holds and secures the piercing member in place so that it can be used. The slidable piercing member cover is non-rotatively coupled to the piercing member base to slide over and cover the piercing member, resulting in the disablement of the piercing assembly. The rotatable piercing member collar is rotatably coupled to the piercing member base and the slidable piercing member cover so that when the rotatable piercing member collar is rotated relative to the piercing member base and the slidable piercing member cover, the slidable piercing member cover slides over and covers the piercing member to disable the disabling piercing assembly.

In particular embodiments, the piercing member base includes stationary supports, and the slidable piercing member cover includes support tabs that engage with the stationary supports to substantially inhibit rotational movement of the slidable piercing member cover relative to the piercing member base. In further embodiments, the rotatable piercing member collar includes slanted channels and lock seats, and the slidable piercing member cover includes twist tabs that engage with the slanted channels to slide the slidable piecing member cover over the piercing member as the rotatable piercing member collar is rotated. The twist tabs engage with the lock seats when the piercing member is covered to prevent the slidable piercing member cover from sliding back down to uncover the piercing member after the disabling piercing assembly is disabled.

In preferred embodiments, the disabling piercing assembly further includes a protective piercing member cap to protect the piercing member prior to use. Also, the piercing member base includes a threaded base for attachment to a device selected from syringes and pen-type injectors.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
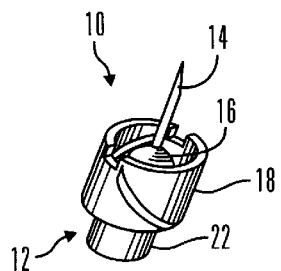
FIG. 1 is a perspective view of a disposable, disabling safety needle in accordance with an embodiment of the present invention.

As shown in the drawings for purposes of illustration, the invention is embodied in a disposable, disabling safety needle. In preferred embodiments of the present invention, the disposable, disabling safety needle is used for an injection with a syringe or pen-type injector and then discarded. However, it will be recognized that further embodiments of the present invention may be used with other types of invasive delivery or transfer devices, such as IV drip systems, lancets or other invasive devices that utilize sharp invasive implements, piercing members, or the like, for delivering substances into or obtaining samples from the body. In still further embodiments of the present invention, the disposable, disabling safety needles may be used in other applications where needles are required to transfer fluid from one location to another, such as between medication vials, adding medication to IV drip bags, or the like.

Embodiments of the present invention provide a relatively passive system for disabling a used needle and safe-guarding the needle from re-use and accidental contact with a user. The disposable, disabling safety needle utilizes an essentially continuous rotation during removal of the needle from the syringe, pen-type injector, or the like, for disabling and enclosing the needle, which does not rely on an entire range of complex human activity. The use of an already existing rotation motion increases compliance with bio-hazard disposal protocols to improve public safety in general and to aid in the control of infectious diseases. Use of the disabling feature of these safety needles, for legitimate medical purposes after use on a single device, helps prevent the needles from becoming available for illegal purposes (such as IV drug abuse and the like). Thus, embodiments of the safety needle are primarily directed to a safety improvement in disposable needles for syringes, pen-type injectors, or the like, that utilizes a self-encapsulating needle to effectively eliminate the dangers of cross-contamination through accidental needle sticks or the possibility of a subsequent injection being given with a removed needle. Preferably, after use, the rotation motion of this safety needle as it is unscrewed from the device in which it is used slides a permanent, non-removable protective cover up and over the needle point to enclose the needle point so that is can no longer be used. Therefore, embodiments of the safety needle operate reliably and efficiently to provide protection from needle re-use as well as from accidental needle sticks.

Generally, embodiments of the safety needle can be manufactured in all of the present disposable syringe or pen-type injector sizes and may be useable for a variety of medical capacities, with various needle gauges, and for different medication applications.

A disposable, disabling safety needle 10 in accordance with an embodiment of the present invention is shown in FIGS. 1–17. The needle 10 includes a needle base 12, a needle 14, a slidable needle cover 16, a rotatable needle collar 18, and a protective needle cap 20.

In preferred embodiments, the needle base 12, slidable needle cover 16, rotatable needle collar 18 and protective needle cap 20 are manufactured from a clear or opaque polymer material that is certified for use in medical devices and needles. During the initial stage of manufacturing, the needle base 12, slidable needle cover 16, rotatable needle collar 18 and protective needle cap 20 are injection molded to facilitate proper sterilization and later assembly. In alternative embodiments, the needle base 12, slidable needle cover 16, rotatable needle collar 18 and protective needle cap 20 may be formed out of other materials, such as plastic, glass, metal, composites, a combination of materials, and the like, and may be formed by casting or die striking, or from multiple pieces that are either snap fitted or adhered together, or the like.

In preferred embodiments, the needle 14 is made from hollow stainless steel and comes in standard needle gauges. In alternative embodiments, the needle may be solid, such as a lancet or the like or may be made from other materials such as, plastics, glass, ceramics, other metals or the like.

Figure 2:
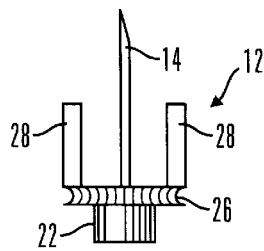
FIG. 2 is a side plan view of a needle base in accordance with the embodiment shown in FIG. 1.
Figure 3:
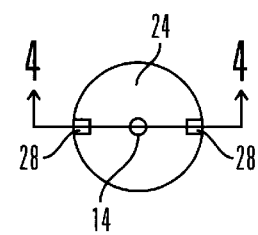
FIG. 3 is a top plan view of a needle base in accordance with the embodiment shown in FIG. 1.
Figure 4:
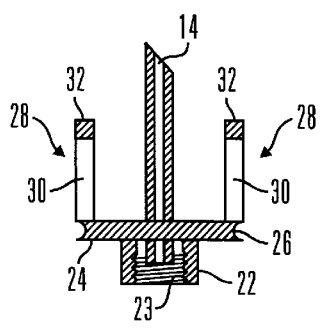
FIG. 4 is a cross-sectional view of a needle base as shown along the line 4—4 in FIG. 3.

As shown in FIGS. 2–4, the needle base 12 holds and secures the needle 14 so that is can be coupled to a syringe, pen-type injector, or the like, so that it can be used for an injection. The needle base 12 includes a threaded base 22 having threads 23 that are used to secure the disabling safety needle 10 to a syringe, pen-type injector, or the like. The threaded base 22 and threads 23 are preferably formed to fit existing standardized syringes, pen-type injectors, or the like. However, in alternative embodiments, the threaded base and threads may be modified to fit non-standard devices and may be secured by other methods, such as friction, snap fits or the like.

Attached to a top of the threaded base 22 is a base plate 24 that includes a circumferential groove 26 or slot that is used to match with a corresponding protrusion on the rotatable needle collar 18 to rotatably secure the rotatable needle collar 18 to the needle base 12. In alternative embodiments, the circumferential groove 26 may be replaced with a circumferential protrusion to match a corresponding groove on the rotatable needle collar 18, with the shape of the grooves and protrusions being selected to facilitate assembly of the disposable, disabling safety needle 10 and rotation of the rotatable needle collar 18. The base plate 24 also has a center bore that is used to secure the needle 14 to the needle base 12. In preferred embodiments, the needle 14 is secured at its approximate midpoint so that one end may be used for piercing the skin, or the like, and the other may be used for piecing a septum on the device to which the disposable, disabling safety needle 10 is attached.

As shown in FIGS. 2–4, attached to the base plate 24 are a pair stationary supports 28 that are used to prevent the slidable needle cover 16 from rotating as the rotatable needle collar 18 is used to slide the slidable needle cover 16 over the needle 14 after use. The stationary supports 28 are also used to secure the protective needle cap 20 to the disposable, disabling safety needle 10 prior to use to prevent accidental needle sticks while securing the disposable, disabling safety needle to a syringe, pen-type injector, or the like. As shown in FIG. 4, preferred embodiments of the stationary supports 28 are formed from a pair of support members 30 attached at one end to the base plate 24 and connected together at the other end by a connector bar 32 to form a channel to couple to the slidable needle cover 16 and protective needle cap 20. In alternative embodiments, the stationary supports 28 may have a back member (not shown) to close off the side of the support members 30 located adjacent the rotatable needle collar 18. This provides additional rigidity and may facilitate injection molding of the needle base 12. In preferred embodiments, there are a pair of stationary supports 28; however, in alternative embodiments, more stationary supports may be used, so long as the slidable needle cover 16 is able to slide up to properly cover the needle 14 and the slidable needle cover 16 is prevented from rotating. In preferred embodiments, the stationary supports 28 will be flush with the upper surface of the rotatable needle collar 18. However, in alternative embodiments, the stationary supports may be recessed to minimize contact with the skin during an injection.

Figure 5:
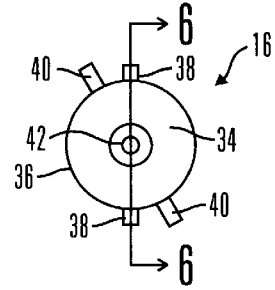
FIG. 5 is a top plan view of a slidable needle cover in accordance with the embodiment shown in FIG. 1.
Figure 6:
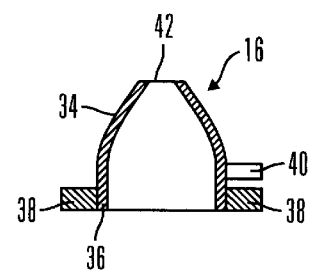
FIG. 6 is a cross-sectional view of a slidable needle cover as shown along the line 6—6 in FIG. 5.

As shown in FIGS. 5 and 6, the slidable needle cover 16 is used to mate with the stationary supports 28 of the needle base 12 and the rotatable needle collar 18 to cover and disable the needle 14 from further use as the disposable, disabling safety needle 10 is removed from a syringe, pen-type injector, or the like. In preferred embodiments, the slidable needle cover 16 has a tapered upper section 34 (to minimize contact with the skin or spreading of the skin during an injection or penetration with the needle 14) and a generally cylindrical base section 36. Preferably, the tapered upper section 34 is formed to have a diameter, near the needle 14, that is similar to the tapered bases, securing conventional that are fixed to a needle base without a cover. However, in alternative embodiments, different tapered shapes may be used, with the shape of the upper section being dependent on the use to which the disposable, disabling safety needle 10 is put.

As shown in FIGS. 5 and 6, the cylindrical base section 36 of the slidable needle cover 16 includes a pair of support tabs 38 that fit into the channel formed in the corresponding stationary supports 28 of the needle base 12. In preferred embodiments, there are a pair of support tabs 38; however, in alternative embodiments, the number of support tabs is increased to correspond in number to the number of stationary supports 28 on the needle base 12. The support tabs 38 permit the slidable needle cover 16 to slide up or down in the channel formed between the support members 30, and the support tabs 38 are prevented from leaving the channel by contacting the connecting bar 32 at the upper end of the channel formed in the stationary supports 28. This allows the slidable needle cover 16 to slide down over the needle 14 during assembly and up over the needle 14 when disabling the needle 14 as the disposable, disabling safety needle 10 is removed from the syringe, pen-type injector, or the like.

Also, attached to the juncture of the tapered upper section 34 and generally cylindrical base 36 are a pair of twist tabs 40 that mate with a corresponding pair of slanted channels on the rotatable needle collar 18. Generally, the twist tabs 40 are longer and stick out further from the slidable needle cover 16 then the support tabs 38, since they engage with the rotatable needle collar 18 that has a diameter that surrounds the stationary supports 28 of the needle base 12 (see FIGS. 10 and 11). The twist tabs 40 move the slidable needle cover 16 up over the needle 14 as the rotatable needle collar 18 is rotated when the disposable, disabling safety needle 10 is removed from the syringe, pen-type injector, or the like. The twist tabs 40 also mate with lock seats on the rotatable needle collar 18 to prevent the slidable needle cover 16 from being lowered to expose the needle 14 after the disposable, disabling safety needle 10 has been disabled. In the illustrated embodiments, the twist tabs 40 are angularly positioned relatively close to the support tabs 38. However, in alternative embodiments, the twist tabs 40 may be positioned at any angular position (e.g., between 45° to 90°) to increase stability of the slidable needle cover 16.

The slidable needle cover 16 also includes a needle port 42 at the top of the tapered upper section 34 that is sized to the diameter of the needle, which permits the needle 14 to slide through the slidable needle cover 16.

Figure 7:
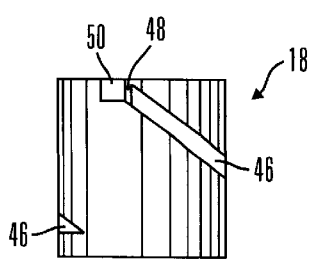
FIG. 7 is a side plan view of a rotatable needle collar in accordance with the embodiment shown in FIG. 1.
Figure 8:
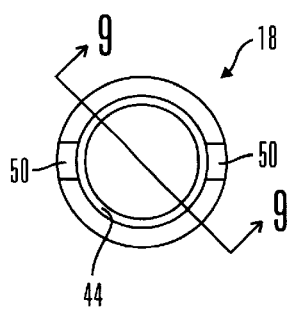
FIG. 8 is a top plan view of a rotatable needle collar in accordance with the embodiment shown in FIG. 1.
Figure 9:
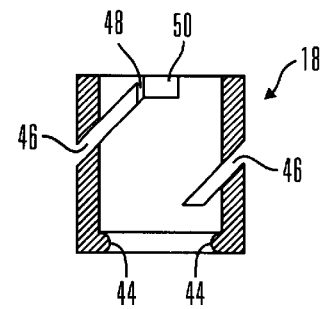
FIG. 9 is a cross-sectional view of a rotatable needle collar as shown along the line 9—9 in FIG. 8.

As shown in FIGS. 7–9, the rotatable needle collar 18 is generally cylindrical and has a protrusion 44 that is shaped to fit the groove 26 in the base plate 24 of the needle base 12 to rotatably connect the rotatable needle collar 18 to the needle base 12 so that the rotatable needle collar 18 can be rotated freely in any direction. In preferred embodiments, the protrusion 44 is generally semi-circular; however, in alternative embodiments, different shapes may be used or a groove may be used so long as the protrusion or groove corresponds to the shape on the base plate 24 of the needle base 12. In preferred embodiments, the rotatable needle collar 18 includes a pair of slanted channels 46 shaped to receive the twist tabs 40 of the slidable needle cover 16. The slanted channels are angled and orientated to force the slidable needle cover 16 up when the disposable, disabling safety needle 10 is removed from the syringe, pen-type injector, or the like. On the other hand, the slanted angle and orientation of the slanted channels 46 performs the reverse function of holding the slidable needle cover 16 down against the base plate 24 of the needle base 12 when the disposable, disabling safety needle 10 is attached to the syringe, pen-type injector, or the like. When the slidable needle cover 16 is held against the base plate 24, rotation of the rotatable needle collar 18 is inhibited permitting the disposable, disabling safety needle to be threaded onto the syringe, pen-type injector, or the like, in a normal matter without interference from a continuously rotating collar 18.

As shown in FIGS. 7–9, at the upper end of the slanted channel 46 is a closing flap 48 leading to a lock seat 50 that permits the twist tab 40 of the slidable needle cover 16 to pass out of the slanted channel 46 into the lock seat 50 and prevent the twist tab 40 from re-entering the slanted channel 46. The closing flap 46 works in the following manner. As the twist tab 40 is moved up the slanted channel 46 when the rotatable needle collar 18 is rotated relative to the slidable needle cover 16, the twist tab 40 encounters and presses against the closing flap 48. As the rotational movement continues, the closing flap 48 moves up and out of the way of the twist tab 40 so that the twist tab 40 moves into the lock seat 50. As the twist tab 40 passes by the closing flap 48, the closing flap reseats itself and closes off the end of the slanted channel 46 so that the twist tabs 40 are retained in the lock seat 50 and the needle 14 remains covered by the slidable needle cover 16. If a user tries to rotate the rotatable needle collar 18 in the opposite direction, the closing flap 48 is again contacted and prevents the twist tab 40 from re-entering the slanted channel 46. If a user attempts to force the twist tab 40 past the closing flap 48 into the slanted channel 46, the closing flap 48 will fold back into the slanted channel 46; however, insufficient width in the slanted channel 46 will remain since the closing flap 48 will be blocking a portion of the slanted channel 46, and this will also prevent the twist tab 40 from re-entering the slanted channel 46. Thus, the twist tabs 40 remain in the lock seat 50, once they pass out of the slanted channels 46. In preferred embodiments, there are a pair of slanted channels 46, closing flaps 48 and lock seats 50. However, in alternative embodiments, there may be more slanted channels, closing flaps and lock seats so long as they correspond in number to the number of twist tabs on the slidable needle cover 16. In preferred embodiments, the lock seats 50 are located on the upper surface of the rotatable needle collar 18. However, in alternative embodiments, the lock seats may be located below the upper surface of the rotatable needle collar 18 and form an enclosed portal or the like. This might provide additional structural rigidity to the rotatable needle collar 18, since there would be a solid ring of material along the top of the rotatable needle collar 18 that is not interrupted by a break from the lock seat 50 that leads to the slanted channels 46.

Figure 14:
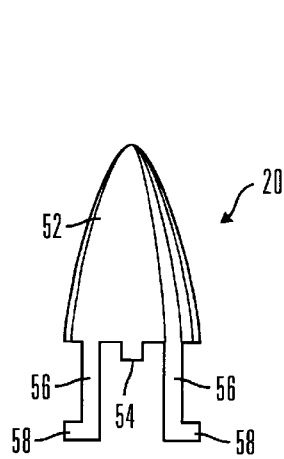
FIG. 14 is a side plan view of a protective needle cap in accordance with the embodiment shown in FIG. 1.
Figure 15:
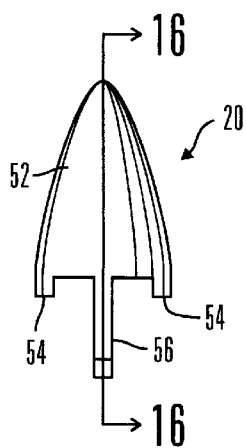
FIG. 15 is another side plan view of a protective needle cap rotated 90° to the view shown in FIG. 14.
Figure 16:
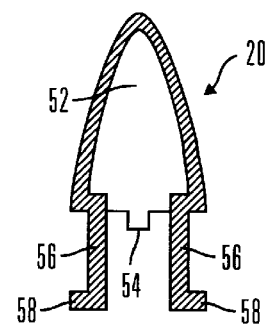
FIG. 16 is a cross-sectional view of a protective needle cap as shown along the line 16—16 in FIG. 15.

As shown in FIGS. 14–16, the protective needle cap 20 is used to cover the needle 14 prior to use and prevent premature disabling of the disposable, disabling safety needle 10 during installation on a syringe, pen-type injector, or the like. The protective needle cap 20 has a conical upper portion 52 sized to cover and protect the needle 14 prior to use and prevent pricking by the needle 14 during installation. In alternative embodiments, the upper portion may be other shapes, such as truncated cones, closed cylinders or the like. The protective needle cap 20 also include seat tabs 54 that engage with the lock seats 50 of the rotatable needle collar 18 to assist the protective needle cap 20 in resisting rotational movement during installation of the disposable, disabling safety needle 10. Attached to the protective needle cap 20 just below the seat tabs 54 are retaining legs 56 that terminate in lock tabs 58. The retaining legs 56 are sized to a sufficient length that permits the lock tabs 58 to enter and be retained in the channel of the stationary supports 28 of the needle base 12 and to contact the top of the support tabs 38 of the slidable needle cover 16 when the slidable needle cover 16 is positioned against the base plate 24 of the needle base 12 and the seat tabs 54 are seated in the lock seats 50 of the rotatable needle collar 18. Once the lock tabs 58 are positioned in the channel of the stationary supports 28, the slidable needle cover 16 is inhibited from sliding up over the needle 14 prematurely until after the protective needle cap 20 is removed. In alternative embodiments, the retaining legs 56 may include additional lock tabs that engage with the connecting bar 32 of the stationary support to further inhibit removal of the protective needle cap 20 and sliding up of the slidable needle cover 16.

Figure 10:
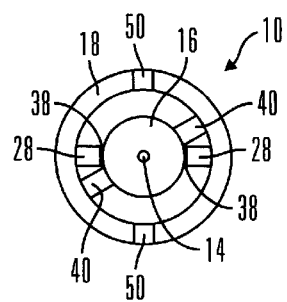
FIG. 10 is a top plan view of a disposable, disabling safety needle prior to disabling in accordance with the embodiment shown in FIG. 1.
Figure 12:
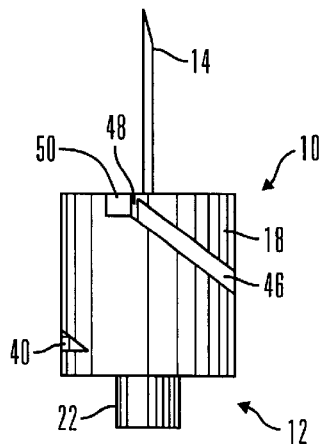
FIG. 12 is a side plan view of a disposable, disabling safety needle prior to disabling in accordance with the embodiment shown in FIG. 1.
Figure 17:
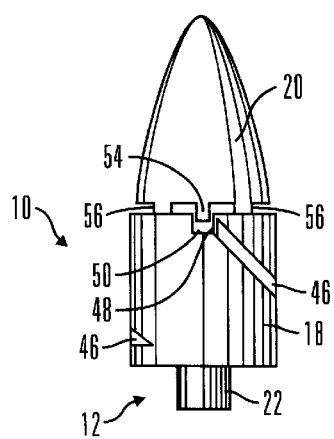
FIG. 17 is a side plan view of a disposable, disabling safety needle with a protective needle cap prior to attachment to a syringe, pen-type injector or the like in accordance with the embodiment shown in FIG. 1.
Figure 18:
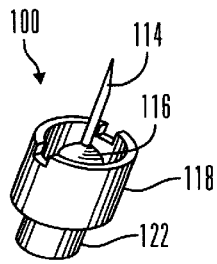
FIG. 18 is a perspective view of a disposable, disabling safety needle in accordance with another embodiment of the present invention.

To assemble the disposable, disabling safety needle 10, the assembler couples the rotatable needle cover 18 to the needle base 12 and the slidable needle cover 16 is coupled to both the needle base 12 and the rotatable needle collar 18 to finish the disposable, disabling safety needle. One preferred method of assembly is to first squeeze the slidable needle cover 16 to deform its shape sufficiently to permit the twist tabs 40 to fit within the interior diameter of the rotatable needle collar 18. Once inside the rotatable needle collar 18, the twist tabs 40 are aligned with the slanted channels 40, and the deformed slidable needle cover 16 is released so that the twist tabs 40 enter the slanted channels 46. Next the rotatable needle collar 18 is passed over the stationary supports 28 of the needle base 12 with the protrusion 42 positioned closest to the base plate 24. The shape of the slidable needle cover 16 is then deformed slightly to permit the support tabs 38 of the slidable needle cover 16 to enter the channel in the stationary supports 28 of the needle base 12. Since the support tabs 38 are shorter than the twist tabs 40, the slidable needle cover 16 is not deformed to the same degree in as the previous step, and the support tabs 38 can be inserted into the channel in the stationary supports 28 without withdrawing the twist tabs 40 from the slanted channels 46. Once the support tabs 38 are seated in the channel of the stationary supports 28, the rotatable needle collar is pressed down against the base plate so that the protrusion 42 of the rotatable needle collar 18 engages with the corresponding groove 26 of the base plate 24 to secure the rotatable needle collar 18 to the needle base 12. Next, the rotatable needle collar is rotated to force the slidable needle cover 16 to rest against the base plate 24 of the needle base 12. The disposable, disabling safety needle 10 is then completed as shown in FIGS. 10 and 12. Finally, the protective needle cap 20 is positioned with the seat tabs 54 over the lock seats 50 of the rotatable needle collar 18. The retaining legs 56 are deformed towards each other so that the lock tabs 58 can engage with the channel in the stationary supports 28 of the needle base 12. The restraining legs 56 are then released and the protective needle cap 20 is slid down until the lock tabs 58 contact the top of the support tabs 38 and the seat tabs 54 contact the bottom of the lock seats 50. As a final step, the protective needle cap 20 may be plastic welded, or otherwise secured, to the rotatable needle collar 18 to prevent inadvertent removal of the protective needle cap 20 prior to use and to help resist rotation of the rotatable needle collar 18 during installation of the disposable, disabling safety needle 10. The disposable, disabling safety needle 10 is then ready for transport and installation, as shown in FIG. 17. During assembly, the needle 14 may be attached prior to attaching the other components or after assembly and prior to attaching the protective needle cap 20.

To use the disposable, disabling safety needle 10, the user holds the syringe, pen-type injector, or the like, and threads the threaded base 22 of the needle base 12 onto the syringe, pen-type injector, or the like, with the protective needle cap 20 affixed to the disposable, disabling safety needle 10. The rotatable needle collar 18 is inhibited from rotating during installation, since the protective needle cap 20 holds the collar 18 in position, and the slanted channels 46 press the slidable needle cover 16 in the base plate 24 to further resist rotation. The user then removes the protective needle cap 20 and proceeds to use the needle 14.

Figure 11:
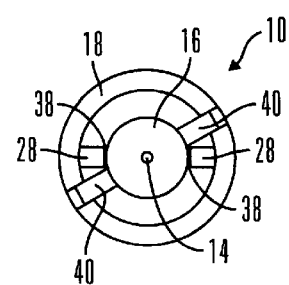
FIG. 11 is a top plan view of a disposable, disabling safety needle after disabling in accordance with the embodiment shown in FIG. 1.
Figure 13:
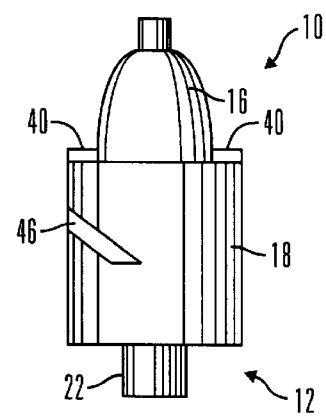
FIG. 13 is a side plan view of a disposable, disabling safety needle after disabling in accordance with the embodiment shown in FIG. 1.

After the needle 14 has been used, the user grasps the rotatable needle collar 18 and un-threads the disposable, disabling safety needle 10 to remove it from the syringe, pen-type injector, or the like. As the user unthreads the disposable, disabling safety needle from the positions shown in FIGS. 10 and 12, the rotatable needle collar 18 rotates and forces the twist tabs 40 in the slanted channels 46 up towards the closing flap 48 and the lock seat 50 on the rotatable needle collar 18. As the twist tabs 40 are moved up, the slidable needle cover 16 slides up and covers the needle 14 to disable the disposable, disabling safety needle 10 from further use, as shown in FIGS. 11 and 13. Once the twist tabs 40 are positioned in the lock seats 50, the rotatable needle collar 18 is inhibited from further rotation as the twist tabs 40 bear against the sides of the lock seats 50. When the rotatable needle collar 18 is inhibited from rotating, the disposable, disabling safety needle 10 can be un-threaded from the syringe, pen-type injector, or the like, in a normal manner. The needle 14 is now shielded from accidental pricks by the slidable needle cover 16, which is now locked in place, and the disposable, disabling safety needle 10 can be disposed of in a proper container.

FIGS. 18–23 illustrate detailed drawings of a disposable, disabling safety needle in accordance with another embodiment of the present invention. Many of the parts are similar to those described above (having like numbers, with the addition of 100) and represent parts that operate similarly to the parts described above. Therefore, a detailed description of these similar parts is omitted. As shown in FIGS. 18–23, the disposable, disabling safety needle 100 includes a needle base 112, a needle 114, a slidable needle cover 116, and a rotatable needle collar 1 18. Many of the parts have been changed in this embodiment to facilitate assembly and structural stability after the disposable, disabling safety needle 100 has been disabled.

Figure 20:
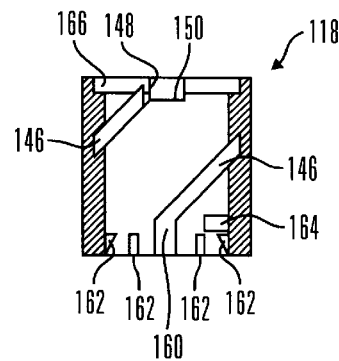
FIG. 20 is a cross-sectional view of a rotatable needle collar as shown along the line 20—20 in FIG. 19.

As shown in FIG. 20, the slanted channels 146 no longer extend entirely through the rotatable needle collar 118. This provides a smooth exterior surface and minimizes interference with the twist tabs 40 and the user's fingers as the disposable, disabling safety needle 100 is removed from the syringe, pen-type injector, or the like. In addition, the slanted channels 146 have been extended with a vertical channel segment 160 to facilitate assembly of the disposable, disabling safety needle 100.

Figure 19:
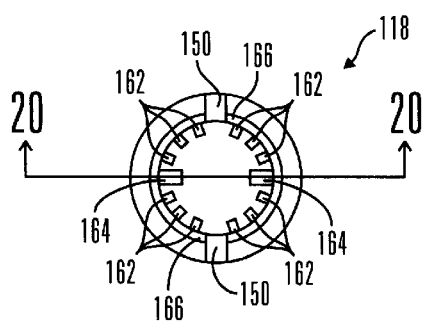
FIG. 19 is a top plan view of a rotatable needle collar in accordance with the embodiment shown in FIG. 18.

As shown in FIGS. 19 and 20, the protrusion 44 of the other embodiment of the rotatable needle collar 18 has been replaced slide easily over the 162 that are adapted to slide easily over the base plate 124 of the needle base 112 and engage with the circumferential groove of the base plate to permit the rotatable needle collar 118 to rotate. The rotatable needle collar 1 18 also includes a pair of lock teeth 164 that are adapted to engage with a recess on the surface of the base plate 124 to help resist rotational movement of the rotatable needle collar 118, once the disposable, disabling safety needle 100 is disabled.

As shown in FIGS. 19 and 20, the top of the rotatable needle collar 118 includes a seat 166 that is adapted to receive and hold the base of the slidable needle cover 116, once the slidable needle cover 116 has been slid over the needle 114.

Figure 21:
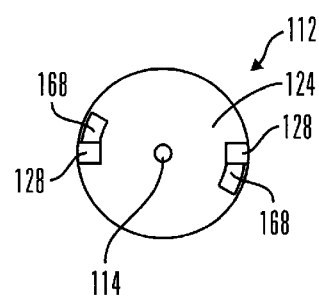
FIG. 21 is a top plan view of a needle base in accordance with the embodiment shown in FIG. 18.

As shown in FIG. 21, the base plate 124 of the needle base 112 includes recesses 168 to receive the lock teeth 164 of the rotatable needle collar as the twist tabs 140 of the slidable needle cover 116 engage with the lock seats 150. Once the lock teeth 164 are engaged with the recesses 168, the rotatable needle collar 118 cannot be rotated backward and the rotatable needle collar 118 is further prevented from rotating forward as the lock teeth 164 bear against the sides of the recesses 168. This also reduces the load placed on the stationary supports 128 as they resist rotation of the rotatable needle collar 118 via the support tabs 138 of the slidable needle cover 116.

Figure 22:
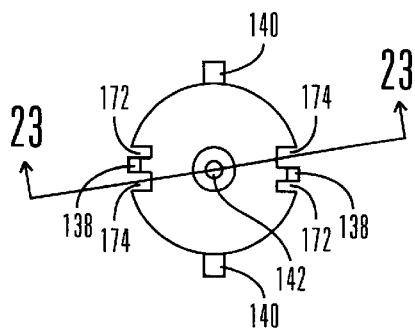
FIG. 22 is a top plan view of a slidable needle cover in accordance with the embodiment shown in FIG. 18.
Figure 23:
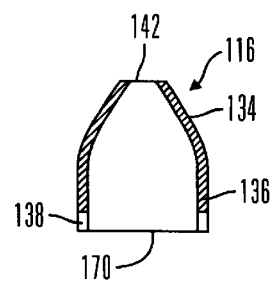
FIG. 23 is a cross-sectional view of the slidable needle cover as shown along the line 23—23 in FIG. 22.

FIGS. 22 and 23 show the slidable needle cover 116 in accordance with this embodiment of the present invention. The slidable needle cover 116 has a larger diameter than the slidable needle cover 16 and includes a base 170 adapted to fit in the seat 166 of the rotatable needle collar 118 after the twist tabs 40 have entered the lock seats 150 of the rotatable needle collar 118. To accommodate the larger diameter, the support tabs 138 are recessed into the diameter of the base portion 136 of the slidable needle cover 116. The slidable needle cover 116 includes a gap 172 that permits the stationary members 30 of the stationary supports 128 to fit around the support tabs 138. The gap 172 provides a bearing surface from the exposed wall of the slidable needle cover 116 to further resist rotational movement of the slidable needle cover 116. The slidable needle cover 116 also includes teeth gaps 174 that are sized to permit the lock teeth 164 of the rotatable needle collar 118 to pass through the slidable needle cover 116 during assembly.

In preferred embodiments, the slidable needle cover 116 and the rotatable needle collar 118 are made from a substantially rigid material, such as a hard polymer. The needle base 112 is made from a slightly more flexible material to facilitate assembly. However, in alternative embodiments, other materials or rigidities may be used, with the choice being dependent on assembly methods and the use to which the disposable, disabling safety needle 100 will be put.

To assemble the disposable, disabling safety needle 100, the stationary supports 28 are bent out slightly to permit insertion of the support tabs 138 of the slidable needle cover 116. The slidable needle cover 116 is then slid down the channel in the stationary supports 128 until the base 170 of the slidable needle cover 116 contacts the base plate 124 of the needle base 112. Next, the rotatable needle collar is positioned over the needle base 112 and the slidable needle cover 116, so that the twist tabs 140 of the slidable needle cover 116 line up with the vertical channel segments 160 of the rotatable needle collar 118. This compresses the base 170 of the slidable needle cover 116 inward slightly so that it will fit within the rotatable needle collar 118 with a slight interference fit. Then the rotatable needle collar 118 is pressed down against the base plate 124 of the needle base 112 so that the teeth 162 of the rotatable needle collar 118 pass over the edge of the base plate 124 and seat in the circumferential groove of the base plate 124 to permit rotation of the rotatable needle collar 118. At the same time, the twist tabs 140 move from the vertical channels segment 160 into the slanted channel 146 of the rotatable needle collar 118. Also, the lock teeth 164 pass through the gap 174 in the slidable needle cover 116 and rest against the surface of the base plate 124 to permit rotational movement of the rotatable needle collar 118 until the lock teeth 164 engage with the recess 168 of the base plate 124 of the needle base 112 as the disposable, disabling safety needle 100 is disabled. The needle 114 may be attached either prior to assembly of the other components or just prior to attachment of the protective needle cap. Finally, the protective needle cap is attached to the disposable, disabling safety needle 100 to facilitate transport and installation.

To use the disposable, disabling safety needle 100, the user holds the syringe, pen-type injector, or the like, and threads the threaded base 122 of the needle base 112 onto the syringe, pen-type injector, or the like, with the protective needle cap affixed to the disposable, disabling safety needle 100. The rotatable needle collar 118 is inhibited from rotating during installation, since the protective needle cap holds the collar 118 in position and the slanted channels 146 press the slidable needle cover 116 in the base plate 124 to further resist rotation. The user then removes the protective needle cap and proceeds to use the needle 114 as usual.

After the needle 114 has been used, the user grasps the rotatable needle collar 118 and unthreads the disposable, disabling safety needle 100 to remove it from the syringe, pen-type injector, or the like. As the user unthreads the disposable, disabling safety needle 100, the rotatable needle collar 118 rotates and forces the twist tabs 140 in the slanted channels 146 up towards the closing flap 148 and the lock seat 150 on the rotatable needle collar 118. As the twist tabs 140 are moved up the slidable needle cover 116 slides up and covers the needle 114 to disable the disposable, disabling safety needle 100 from further use. At the same time, as the twist tabs 140 enter the lock seats 150, the lock teeth 164 are pressed down and engage with the recesses 168 of the base plate 124 to resist further rotational movement of the rotatable needle collar 118. Once the twist tabs 140 are positioned in the lock seats 150, the rotatable needle collar 118 is inhibited from further rotation as the twist tabs 140 bear against the sides of the lock seats 150 and the lock teeth 164 bear against the sides of the recesses 168. Also, as the twist tabs 140 enter the locking seats 150, the base 170 of the slidable needle cover 116 expands to fit the seat 166 on the rotatable needle collar 118 to resist attempts to slide the slidable needle cover 116 down to expose the needle 114. When the rotatable needle collar 118 is inhibited from rotating, the disposable, disabling safety needle 100 can be unthreaded from the syringe, pen-type injector, or the like, in a normal manner. The needle 114 is now shielded from accidental pricks by the slidable needle cover 116, which is now locked in place, and the disposable, disabling safety needle 100 can be disposed of in a proper container.

While the description above refers to particular embodiments of the present invention, it will be understood that many modifications may be made without departing from the spirit thereof The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A disabling piercing assembly comprising:

a piercing member;

a piercing member base that holds and secures the piercing member in place;

a slidable piercing member cover non-rotatively coupled to the piercing member base to slide over and cover the piercing member to disable the disabling piercing assembly; and a rotatable piercing member collar rotatably coupled to the piercing member base and the slidable piercing member cover, wherein when the rotatable piercing member collar is rotated relative to the piercing member base and the slidable piercing member cover, the slidable piercing member cover slides over and covers the piercing member to disable the disabling piercing assembly.

2. A disabling piercing assembly according to claim 1, wherein the piercing member is a needle.

3. A disabling piecing assembly according to claim 1, wherein the piercing member base includes stationary supports, and wherein the slidable piercing member cover includes support tabs that engage with the stationary supports to substantially inhibit rotational movement of the slidable piercing member cover relative to the piercing member base.

4. A disabling piercing assembly according to claim 1, wherein the rotatable piercing member collar includes slanted channels and lock seats, and wherein the slidable piercing member cover includes twist tabs that engage with the slanted channels to slide the slidable piecing member cover over the piercing member as the rotatable piercing member collar is rotated, and wherein the twist tabs engage with the lock seats when the piercing member is covered to prevent the slidable piercing member cover from sliding down to uncover the piercing member after the disabling piercing assembly is disabled.

5. A disabling piercing assembly according to claim 1, further including a protective piercing member cap to protect the piercing member prior to use.

6. A piercing member assembly according to claim 1, wherein the piercing member base includes a threaded base for attachment to a device selected from the group consisting of syringes and pen-type injectors.

7. A disabling needle assembly comprising:

a needle;

a needle base that holds and secures the needle in place, wherein the needle base includes stationary supports;

a slidable needle cover non-rotatively coupled to the needle base to slide over and cover the needle to disable the disabling needle assembly, wherein the slidable needle cover includes support tabs that engage with the stationary supports of the needle base to substantially inhibit rotational movement of the slidable needle cover relative to the needle base, and wherein the slidable piercing member cover also includes twist tabs; and a rotatable needle collar rotatably coupled to the needle base and the slidable needle cover, wherein when the rotatable needle collar is rotated relative to the needle base and the slidable needle cover, the slidable needle cover slides over and covers the needle to disable the disabling needle assembly, wherein the rotatable piercing member collar includes slanted channels and lock seats, wherein the twist tabs of the slidable needle cover engage with the slanted channels to slide the slidable needle cover over the needle as the rotatable needle collar is rotated, and wherein the twist tabs engage with the lock seats when the needle is covered to prevent the slidable needle cover from sliding down to uncover the needle after the disabling needle assembly is disabled.

8. A disabling needle assembly according to claim 7, further including a protective piercing member cap to protect the needle prior to use.

9. A needle assembly according to claim 7, wherein the needle base includes a threaded base for attachment to a device selected from the group consisting of syringes and pen-type injectors.

* * * * *